(12) United States Patent
Villarreal et al.

(10) Patent No.: US 11,517,245 B2
(45) Date of Patent: Dec. 6, 2022

(54) METHOD AND SYSTEM FOR DATA SYNCHRONIZATION

(71) Applicant: Cadwell Laboratories, Inc., Kennewick, WA (US)

(72) Inventors: Richard A. Villarreal, West Richland, WA (US); Ivan Amaya, Richland, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 276 days.

(21) Appl. No.: 16/667,570

(22) Filed: Oct. 29, 2019

(65) Prior Publication Data

US 2020/0129081 A1  Apr. 30, 2020

Related U.S. Application Data

(60) Provisional application No. 62/752,675, filed on Oct. 30, 2018.

(51) Int. Cl.
*A61B 5/369* (2021.01)
*A61B 5/374* (2021.01)
*A61B 5/00* (2006.01)

(52) U.S. Cl.
CPC .............. *A61B 5/374* (2021.01); *A61B 5/369* (2021.01); *A61B 5/7203* (2013.01);
(Continued)

(58) Field of Classification Search
CPC ....... A61B 5/7203; A61B 5/72; A61B 5/7225; A61B 5/7285; H03C 3/0908;
(Continued)

(56) References Cited

U.S. PATENT DOCUMENTS

| 751,475 A | 2/1904 | Vilbiss |
| 2,320,709 A | 6/1943 | Arnesen |

(Continued)

FOREIGN PATENT DOCUMENTS

| CN | 104766176 A | 7/2015 |
| DE | 102014008684 A1 | 1/2016 |

(Continued)

OTHER PUBLICATIONS

"Long, S; "Phase Locked Loop Circuits", Apr. 27, 2005". (Year: 2005).*

(Continued)

*Primary Examiner* — Daniel L Cerioni
*Assistant Examiner* — Deirdre M Willgohs
(74) *Attorney, Agent, or Firm* — Novel IP

(57) ABSTRACT

A system for monitoring includes: multiple EEG sensors spatially positioned on a layer of tissue for capturing EEG signals of a patient; multiple amplifiers coupled with the EEG sensors for amplifying the captured signals; and a low frequency oscillator for generating a synchronizing signal which is distributed to the amplifiers for synchronizing the digitization of the captured signals; wherein each amplifier includes: a voltage controlled oscillator for an adjustable frequency reference; an analog to digital converter for converting the amplified signal to a digital value; and a microcontroller for controlling the frequency of the voltage controlled oscillator and operation of the analog to digital converter by using the synchronizing signal.

16 Claims, 6 Drawing Sheets

(52) U.S. Cl.
CPC .......... *A61B 5/7225* (2013.01); *A61B 5/7285* (2013.01); *A61B 5/742* (2013.01)

(58) Field of Classification Search
CPC .. H03C 3/0916; H03C 3/0925; H03C 3/0933; H03C 3/0975; H03C 3/095; H03C 3/0991; H03D 3/241; H03D 3/248; H03J 5/0272; H03J 7/065; H03J 7/285; H03L 7/06; H03L 7/08; H03L 7/085; H03L 7/141; H03L 2207/00; H03L 2207/50; H04L 7/033; H04L 7/0331; Y10S 388/911
USPC .................. 600/544; 375/376; 327/147, 156
See application file for complete search history.

(56) References Cited

U.S. PATENT DOCUMENTS

| | | |
|---|---|---|
| 2,807,259 A | 9/1957 | Guerriero |
| 2,950,437 A | 8/1960 | Stahl |
| 3,165,340 A | 1/1965 | Kuehl |
| 3,659,250 A | 4/1972 | Horton |
| 3,682,162 A | 8/1972 | Colyer |
| 3,985,125 A | 10/1976 | Rose |
| 3,993,859 A | 11/1976 | McNeel |
| 4,155,353 A | 5/1979 | Rea |
| 4,262,306 A | 4/1981 | Renner |
| 4,263,899 A | 4/1981 | Burgin |
| 4,545,374 A | 10/1985 | Jacobson |
| 4,562,832 A | 1/1986 | Wilder |
| 4,616,635 A | 10/1986 | Caspar |
| 4,705,049 A | 11/1987 | John |
| 4,716,901 A | 1/1988 | Jackson |
| 4,743,959 A | 5/1988 | Frederiksen |
| 4,765,311 A | 8/1988 | Kulik |
| 4,817,587 A | 4/1989 | Janese |
| 4,862,891 A | 9/1989 | Smith |
| 4,889,502 A | 12/1989 | Althouse |
| 4,914,508 A | 4/1990 | Music |
| 5,107,845 A | 4/1992 | Guern |
| 5,171,279 A | 12/1992 | Mathews |
| 5,196,015 A | 3/1993 | Neubardt |
| 5,284,153 A | 2/1994 | Raymond |
| 5,284,154 A | 2/1994 | Raymond |
| 5,299,563 A | 4/1994 | Seton |
| 5,377,667 A | 1/1995 | Patton |
| 5,438,989 A | 8/1995 | Hochman |
| 5,462,448 A | 10/1995 | Kida |
| 5,472,426 A | 12/1995 | Bonati |
| 5,474,558 A | 12/1995 | Neubardt |
| 5,540,235 A | 7/1996 | Wilson |
| 5,544,286 A | 8/1996 | Laney |
| 5,560,372 A | 10/1996 | Cory |
| 5,565,779 A | 10/1996 | Arakawa |
| 5,578,060 A | 11/1996 | Pohl |
| 5,601,608 A | 2/1997 | Mouchawar |
| 5,602,585 A | 2/1997 | Dickinson |
| 5,625,759 A | 4/1997 | Freeman |
| 5,648,815 A | 7/1997 | Toba |
| 5,664,029 A | 9/1997 | Callahan |
| 5,681,265 A | 10/1997 | Maeda |
| 5,684,887 A | 11/1997 | Lee |
| 5,728,046 A | 3/1998 | Mayer |
| 5,741,261 A | 4/1998 | Moskovitz |
| 5,766,133 A | 6/1998 | Faisandier |
| 5,772,661 A | 6/1998 | Michelson |
| 5,775,331 A | 7/1998 | Raymond |
| 5,775,931 A | 7/1998 | Jones |
| 5,785,648 A | 7/1998 | Min |
| 5,792,044 A | 8/1998 | Foley |
| 5,795,291 A | 8/1998 | Koros |
| 5,830,150 A | 11/1998 | Palmer |
| 5,847,755 A | 12/1998 | Wixson |
| 5,860,973 A | 1/1999 | Michelson |
| 5,868,668 A | 2/1999 | Weiss |
| 5,885,210 A | 3/1999 | Cox |
| 5,891,147 A | 4/1999 | Moskovitz |
| 5,928,139 A | 7/1999 | Koros |
| 5,928,158 A | 7/1999 | Aristides |
| 5,930,379 A | 7/1999 | Rehg |
| 5,931,777 A | 8/1999 | Sava |
| 5,933,929 A | 8/1999 | Kawakami |
| 5,944,658 A | 8/1999 | Koros |
| 5,954,635 A | 9/1999 | Foley |
| 5,993,385 A | 11/1999 | Johnston |
| 6,004,312 A | 12/1999 | Finneran |
| 6,004,341 A | 12/1999 | Zhu |
| 6,026,180 A | 2/2000 | Wittenstein |
| 6,042,540 A | 3/2000 | Johnston |
| 6,062,216 A | 5/2000 | Corn |
| 6,074,343 A | 6/2000 | Nathanson |
| 6,088,878 A | 7/2000 | Antonucci |
| 6,095,987 A | 8/2000 | Shmulewitz |
| 6,109,948 A | 8/2000 | Kuo |
| 6,116,941 A | 9/2000 | Kuo |
| 6,119,306 A | 9/2000 | Antonucci |
| 6,139,493 A | 10/2000 | Koros |
| 6,152,871 A | 11/2000 | Foley |
| 6,181,961 B1 | 1/2001 | Prass |
| 6,196,969 B1 | 3/2001 | Bester |
| 6,200,331 B1 | 3/2001 | Swartz |
| 6,206,826 B1 | 3/2001 | Mathews |
| 6,210,202 B1 | 4/2001 | Kuo |
| 6,224,545 B1 | 5/2001 | Cocchia |
| 6,236,874 B1 | 5/2001 | Devlin |
| 6,241,548 B1 | 6/2001 | Kuo |
| 6,259,945 B1 | 7/2001 | Epstein |
| 6,264,491 B1 | 7/2001 | Lord |
| 6,266,558 B1 | 7/2001 | Gozani |
| 6,273,740 B1 | 8/2001 | Lord |
| 6,287,322 B1 | 9/2001 | Zhu |
| 6,302,842 B1 | 10/2001 | Auerbach |
| 6,306,100 B1 | 10/2001 | Prass |
| 6,309,349 B1 | 10/2001 | Bertolero |
| 6,325,764 B1 | 12/2001 | Griffith |
| 6,334,068 B1 | 12/2001 | Hacker |
| 6,373,890 B1 | 4/2002 | Freeman |
| 6,425,859 B1 | 7/2002 | Foley |
| 6,450,952 B1 | 9/2002 | Rioux |
| 6,466,817 B1 | 10/2002 | Kaula |
| 6,473,639 B1 | 10/2002 | Fischell |
| 6,500,128 B2 | 12/2002 | Marino |
| 6,535,759 B1 | 3/2003 | Epstein |
| 6,579,114 B2 | 6/2003 | Lord |
| 6,609,018 B2 | 8/2003 | Cory |
| 6,712,795 B1 | 3/2004 | Cohen |
| 6,799,931 B2 | 10/2004 | Kwilosz |
| 6,805,668 B1 | 10/2004 | Cadwell |
| 6,837,716 B1 | 1/2005 | Brazas |
| 6,847,849 B2 | 1/2005 | Mamo |
| 6,851,430 B2 | 2/2005 | Tsou |
| 6,869,301 B2 | 3/2005 | Shimizu |
| 6,870,109 B1 | 3/2005 | Villarreal |
| 6,926,728 B2 | 8/2005 | Zucherman |
| 6,945,933 B2 | 9/2005 | Branch |
| 7,072,521 B1 | 7/2006 | Cadwell |
| 7,089,059 B1 | 8/2006 | Pless |
| 7,104,965 B1 | 9/2006 | Jiang |
| 7,177,677 B2 | 2/2007 | Kaula |
| 7,214,197 B2 | 5/2007 | Prass |
| 7,230,688 B1 | 6/2007 | Villarreal |
| 7,261,688 B2 | 8/2007 | Smith |
| 7,374,448 B2 | 5/2008 | Jepsen |
| 7,470,236 B1 | 12/2008 | Kelleher |
| 7,522,953 B2 | 4/2009 | Kaula |
| 7,713,210 B2 | 5/2010 | Byrd |
| 7,801,601 B2 | 9/2010 | Maschino |
| 7,914,350 B1 | 3/2011 | Bozich |
| 7,963,927 B2 | 6/2011 | Kelleher |
| 7,983,761 B2 | 7/2011 | Giuntoli |
| 8,147,421 B2 | 4/2012 | Farquhar |
| 8,160,694 B2 | 4/2012 | Salmon |
| 8,192,437 B2 | 6/2012 | Simonson |
| D670,656 S | 11/2012 | Jepsen |

(56) References Cited

U.S. PATENT DOCUMENTS

| | | | |
|---|---|---|---|
| 8,323,208 B2 | 12/2012 | Davis | |
| 8,439,703 B2 | 5/2013 | Natoli | |
| 8,876,813 B2 | 11/2014 | Min | |
| 8,942,797 B2 | 1/2015 | Bartol | |
| 8,958,869 B2 | 2/2015 | Kelleher | |
| 9,084,551 B2 | 7/2015 | Brunnett | |
| 9,138,586 B2 | 9/2015 | Eiger | |
| 9,155,503 B2 | 10/2015 | Cadwell | |
| 9,295,401 B2 | 3/2016 | Cadwell | |
| 9,352,153 B2 | 5/2016 | Van Dijk | |
| 9,730,634 B2 | 8/2017 | Cadwell | |
| 10,238,467 B2 | 3/2019 | Cadwell | |
| 2001/0049510 A1 | 12/2001 | Burr | |
| 2002/0007188 A1 | 1/2002 | Arambula | |
| 2002/0009916 A1 | 1/2002 | Lord | |
| 2002/0088098 A1 | 7/2002 | Bouley | |
| 2002/0095080 A1 | 7/2002 | Cory | |
| 2003/0045808 A1 | 3/2003 | Kaula | |
| 2003/0074033 A1 | 4/2003 | Pless | |
| 2004/0030258 A1 | 2/2004 | Williams | |
| 2004/0127810 A1 | 7/2004 | Sackellares | |
| 2004/0192100 A1 | 9/2004 | Shimizu | |
| 2005/0003682 A1 | 1/2005 | Brazas | |
| 2005/0075578 A1 | 4/2005 | Gharib | |
| 2005/0085743 A1 | 4/2005 | Hacker | |
| 2005/0148927 A1 | 7/2005 | Ludin | |
| 2005/0182454 A1 | 8/2005 | Gharib | |
| 2005/0182456 A1 | 8/2005 | Ziobro | |
| 2005/0277844 A1 | 12/2005 | Strother | |
| 2006/0009754 A1 | 1/2006 | Boese | |
| 2006/0085048 A1 | 4/2006 | Cory | |
| 2006/0085049 A1 | 4/2006 | Cory | |
| 2006/0122514 A1 | 6/2006 | Byrd | |
| 2006/0135877 A1 | 6/2006 | Giftakis | |
| 2006/0258951 A1 | 11/2006 | Bleich | |
| 2006/0276720 A1 | 12/2006 | McGinnis | |
| 2007/0016097 A1 | 1/2007 | Farquhar | |
| 2007/0021682 A1 | 1/2007 | Gharib | |
| 2007/0032841 A1 | 2/2007 | Urmey | |
| 2007/0046471 A1 | 3/2007 | Nyalamadugu | |
| 2007/0049962 A1 | 3/2007 | Marino | |
| 2007/0184422 A1 | 8/2007 | Takahashi | |
| 2007/0202005 A1 | 8/2007 | Maschke | |
| 2008/0027507 A1 | 1/2008 | Bijelic | |
| 2008/0058606 A1 | 3/2008 | Miles | |
| 2008/0065144 A1 | 3/2008 | Marino | |
| 2008/0071191 A1 | 3/2008 | Kelleher | |
| 2008/0082136 A1 | 4/2008 | Gaudiani | |
| 2008/0097164 A1 | 4/2008 | Miles | |
| 2008/0108244 A1 | 5/2008 | Jepsen | |
| 2008/0167574 A1 | 7/2008 | Farquhar | |
| 2008/0183096 A1 | 7/2008 | Snyder | |
| 2008/0194970 A1 | 8/2008 | Steers | |
| 2008/0269777 A1 | 10/2008 | Appenrodt | |
| 2008/0281313 A1 | 11/2008 | Fagin | |
| 2008/0312520 A1 | 12/2008 | Rowlandson | |
| 2009/0018399 A1 | 1/2009 | Martinelli | |
| 2009/0088660 A1 | 4/2009 | McMorrow | |
| 2009/0105604 A1 | 4/2009 | Bertagnoli | |
| 2009/0177112 A1 | 7/2009 | Gharib | |
| 2009/0196471 A1 | 8/2009 | Goetz | |
| 2009/0204016 A1 | 8/2009 | Gharib | |
| 2009/0209879 A1 | 8/2009 | Kaula | |
| 2009/0259136 A1 | 10/2009 | Miles | |
| 2009/0279767 A1 | 11/2009 | Kukuk | |
| 2010/0036384 A1 | 2/2010 | Gorek | |
| 2010/0106011 A1 | 4/2010 | Byrd | |
| 2010/0113898 A1 | 5/2010 | Kim | |
| 2010/0152604 A1 | 6/2010 | Kaula | |
| 2010/0168603 A1 | 7/2010 | Himes | |
| 2010/0191305 A1 | 7/2010 | Imran | |
| 2010/0249638 A1 | 9/2010 | Liley | |
| 2010/0286554 A1 | 11/2010 | Davis | |
| 2010/0317931 A1 | 12/2010 | Sarkela | |
| 2010/0317989 A1 | 12/2010 | Gharib | |
| 2011/0082383 A1 | 4/2011 | Cory | |
| 2011/0184308 A1 | 7/2011 | Kaula | |
| 2011/0295579 A1 | 12/2011 | Tang | |
| 2011/0313530 A1 | 12/2011 | Gharib | |
| 2012/0003862 A1 | 1/2012 | Newman | |
| 2012/0071779 A1 | 3/2012 | Sarkela | |
| 2012/0109000 A1 | 5/2012 | Kaula | |
| 2012/0109004 A1 | 5/2012 | Cadwell | |
| 2012/0209082 A1 | 8/2012 | Al-Ali | |
| 2012/0209346 A1 | 8/2012 | Bikson | |
| 2012/0220891 A1 | 8/2012 | Kaula | |
| 2012/0238855 A1* | 9/2012 | Lanning | A61B 5/0017 600/378 |
| 2012/0238893 A1 | 9/2012 | Farquhar | |
| 2012/0265040 A1 | 10/2012 | Ito | |
| 2012/0296230 A1 | 11/2012 | Davis | |
| 2013/0012880 A1 | 1/2013 | Blomquist | |
| 2013/0109996 A1 | 5/2013 | Turnbull | |
| 2013/0138010 A1 | 5/2013 | Nierenberg | |
| 2013/0152657 A1 | 6/2013 | Swinehart | |
| 2013/0204315 A1 | 8/2013 | Wongsarnpigoon | |
| 2013/0253447 A1 | 9/2013 | Ball | |
| 2013/0304407 A1 | 11/2013 | George | |
| 2014/0121555 A1 | 5/2014 | Scott | |
| 2014/0275926 A1 | 9/2014 | Scott | |
| 2014/0276181 A1 | 9/2014 | Sun | |
| 2015/0150512 A1 | 6/2015 | Warner | |
| 2015/0230749 A1 | 8/2015 | Gharib | |
| 2015/0351643 A1 | 12/2015 | Edwards | |
| 2015/0372433 A1 | 12/2015 | Lisogurski | |
| 2016/0000382 A1 | 1/2016 | Jain | |
| 2016/0174861 A1 | 6/2016 | Cadwell | |
| 2016/0270679 A1 | 9/2016 | Mahon | |
| 2016/0328991 A1 | 11/2016 | Simpson | |
| 2017/0100047 A1 | 4/2017 | Edwards | |
| 2018/0117309 A1 | 5/2018 | Rapoport | |
| 2018/0161123 A1 | 6/2018 | Cadwell | |
| 2018/0198218 A1 | 7/2018 | Regan | |
| 2018/0256097 A1 | 9/2018 | Bray | |
| 2018/0296277 A1 | 10/2018 | Schwartz | |
| 2019/0190187 A1 | 6/2019 | Fukazawa | |
| 2020/0022603 A1 | 1/2020 | Cardenas | |
| 2020/0108246 A1 | 4/2020 | Cadwell | |
| 2020/0297282 A1 | 9/2020 | Batzer | |
| 2020/0330772 A1 | 10/2020 | Hartmann-Bax | |

FOREIGN PATENT DOCUMENTS

| | | |
|---|---|---|
| EP | 298268 | 1/1989 |
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| JP | H11513592 A | 11/1999 |
| JP | 2008546509 A | 12/2008 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |
| WO | 2016105571 A1 | 6/2016 |

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

(56) References Cited

OTHER PUBLICATIONS

Dickman, et al., "Techniques in Neurosurgery", National Library of Medicine, 3 (4) 301-307 (1997).
Epstein, et al., "Evaluation of Intraoperative Somatosensory-Evoked Potential Monitoring During 100 Cervical Operations", 18(6):737-747 (1993), J.B. Lippincott Company.
Glassman, et. al., "A Prospective Analysis of Intraoperative Electromyographic Monitoring of Pedicle Screw Placement with Computed Tomographic Scan Confirmation", 20(12):1375-1379.
Goldstein, et. al., "Minimally Invasive Endoscopic Surgery of the Lumbar Spine", Operative Techniques in Orthopaedics, 7 (1):27-35 (1997).
Greenblatt, et. al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", Spine 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. Mar. 1-31, 20, 1998, The Magstim Company Limited.
Kevin T. Foley, et. al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et. al., "Minimally Invasive Vertebral Replacement with Cages in Thoracic and Lumbar Spine", European Journal of Trauma, 2001, No. 6, pp. 292-300.
Lenke, et. al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et. al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et. al., "The NerveSeeker: A System for Automated Nerve Localization", Regional Anesthesia 17:151-162 (1992).
Reidy, et. al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et. al., "The usefulness of Electrical Stimulation for Assessing Pedicle Screw Placements", Journal of Spinal Disorders, 13 (4):283-289 (2000).
U.Schick, et. al., "Microendoscopic lumbar discectomy versus open surgery: an intraoperative EMG study", pp. 20-26, Published online: Jul. 31, 2001 © Springer-Verlag 2001.
Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapters, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al, Electrical characteristics of peripheral nerve stimulators, implications for nerve localization, Dept. of Anesthesia, University of Cincinnati College of Medicine, Cincinnati, OH 45267, pp. 73-77.
Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., "Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.compumedics.com.au/wp-content/uploads/2016/08/AD125-02-Profusion-EEG4-brochureLR.pdf (Year:2017).

(56) References Cited

OTHER PUBLICATIONS

Intelimed Website, "Compumedics Profusion EEG 5 Top Features" accessed online Oct. 9, 2021, available online Sep. 30, 2014 2014).
Deff Corporation, No more confusion about which direction to plug in. A USB cable that can be plugged in both ways is now available. A connector is equipped with an LED indicator to check a charging status of a smartphone. Nov. 6, 2015 (Dec. 28, 2021 Search) Internet URL:https://deff.co.jp/news/dca-mbled (Document showing known technology).
Brainstorm website, https://web.archive.org/web/20180421074035/https://neuroimage.usc.edu/brainstorm/Tutorials/MontageEditor, available online Apr. 21, 2018 (Year: 2018).
Brainstorm website, https://web.archive.org/web/20180330235454/http://neuroimage.usc.edu/brainstorm/Tutorials/CreateProtocol,) available on Mar. 30, 2018 (Year: 2018).
Brainstorm website,https://web.archive.org/web/20180416072211/http://neuroimage.usc.edu/brainstorm/Screenshots ,available on Apr. 16, 2018 (Year: 2018).
Brainstorm website,https://web.archive.org/web/20180411211909/https://neuroimage.usc.edu/brainstorm/Introduction,available on Apr. 11, 2018 (Year: 2018).
Brainstorm website,https://web.archive.org/web/20180505021718/https://neuroimage.usc.edu/brainstorm/Tutorials/Epileptogenicity, available on May 5, 2018 (Year: 2018).

\* cited by examiner

METHOD AND SYSTEM FOR DATA SYNCHRONIZATION

CROSS REFERENCE

The present application relies on U.S. Patent Provisional Application No. 62/752,675, entitled "Method and System for Data Synchronization" and filed on Oct. 30, 2018, for priority, which is herein incorporated by reference in its entirety.

FIELD

The present specification generally relates to the field of neuro-monitoring applications and more specifically to a system and method for synchronizing multiple amplifiers being used in conjunction for amplifying captured electroencephalography (EEG) signals and other biopotential signals.

BACKGROUND

Several medical procedures involve deploying multiple sensors on the human body for the recording and monitoring of data required for patient care. Information, such as vital health parameters, cardiac activity, bio-chemical activity, electrical activity in the brain, gastric activity and physiological data, is usually recorded through on-body or implanted sensors/electrodes which are connected through a wired or wireless link. Typical patient monitoring systems comprise a control unit connected through a wire to one or more electrodes coupled to the specific body parts of the patient. In some applications, such as with pulse oximeter or EKG (electrocardiograph) devices, the electrodes coupled to the body are easily managed as there are not too many. However, with procedures that require a large number of electrodes to be coupled to the human body, the overall set up, placement and management of electrodes is a cumbersome process.

One such procedure that requires a large number of electrodes is Long Term Electroencephalography (EEG) Monitoring (LTM). The purpose of LTM is to detect abnormal brain activity. The presence of abnormal brain activity may require medications and/or surgical interventions. During surgical procedures, LTM may reduce the risk to the patient of iatrogenic damage to the nervous system, and/or to provide functional guidance to the surgeon. Generally, neuromonitoring procedures such as EEG involve a large number of electrodes coupled to the human body. In an EEG procedure, the electrodes are used to record and monitor the electrical activity corresponding to various parts of the brain for detection and treatment of various ailments such as epilepsy, sleep disorders, tumors and coma. EEG procedures are either non-invasive or invasive. In non-invasive EEG, a number of surface electrodes are deployed on the human scalp for recording electrical activity in portions of the underlying brain. In invasive EEG, through surgical intervention, the electrodes are placed directly over sections of the brain, in the form of a strip or grid, or are positioned in the deeper areas of the brain in the form of a depth electrode. All of these electrode types are coupled to a wire lead which, in turn, is connected to a medical system adapted to receive and transmit electrical signals. The electrical activity pattern sensed by various electrodes is analyzed using standard algorithms to localize or spot the portion of brain which is responsible for causing the specific ailment.

The number of electrodes in EEG systems typically varies between 21 and 256. Increasing the number of electrodes in EEG procedures helps decrease the localization error and thus more ably assist the physician to better plan for surgical procedures. Accordingly, advanced EEG systems involve a high density electrode configuration with more than 256 electrodes, possibly 1024 electrodes, for separately mapping the electrical activity corresponding to every portion of the brain. However, the overall set up and verification process becomes more time consuming and error prone as the number of electrodes increases in the EEG procedures.

Most EEG monitoring systems comprise an amplifier for amplifying and digitizing the recorded signals before analyzing the signals. In EEG systems consisting of more than one amplifier, the data from each amplifier must be time synchronized with each other. Data synchronization is important since cerebral events such as seizures have a temporal significance and the EEG signals recorded from a patient may be acquired by more than one amplifier, as is the case in high channel count intracranial EEG monitoring systems. Also, any difference in sample rate between the amplifiers will result in beat frequency noise when the EEG channels in one amplifier are fed as reference to the EEG channels of another amplifier. Beat frequency noise is a periodic artifact added to the EEG signal and is a result of one amplifier's digitizer's (ADCs) sampling a common mode noise of another amplifier as a differential signal. The noise may inhibit analyzing the EEG signals.

Known methods of synchronizing multiple amplifiers include running multiple synchronizing clocks and signals from one amplifier to another or using high precision temperature controlled oscillators in each of the amplifiers, the latter of which requires extremely stable clock oscillators that are typically temperature controlled and an order of magnitude higher in cost than a voltage controlled oscillator, require much more power than a voltage controlled oscillator, and are also physically much larger in size.

The other method of synchronizing the data from different amplifiers comprises sharing the sample clocks of the amplifiers and sharing the 'convert start' signals among all the analog to digital converters (ADC) of all the amplifiers. Though it is possible to share such signals between all of the amplifiers, this is not a desirable topology because specialized and high current consumption equipment and cables would be required to do so and also because the ADC signals can be corrupted by electromagnetic interference, resulting in unexpected functioning of the ADCs.

Hence what is needed is a less complex method of synchronizing the data acquisition from multiple amplifiers than that provided by prior art. What is also needed is a method of synchronization that does not require specialized components, is cost effective and is not susceptible to interference from electrostatic discharge (ESD) interference, electric fast transient (EFT) interference, or other electromagnetic interferences. Such a method would preferably eliminate the need for distributing data from a high speed clock to each of the amplifiers. Distribution of high speed clock data between amplifiers is not desirable since this requires differential circuitry and cabling, and is susceptible to interference from ESD, EFT, and other electromagnetic interference.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a system for monitoring EEG signals comprising: a plurality of EEG sensors positioned on a layer of tissue for capturing EEG signals of a patient; at least one amplifier coupled to each of the plurality of EEG sensors, wherein the at least one amplifier is configured to amplify the captured EEG signals; and a first oscillator configured to generate a synchronizing signal; wherein the at least one amplifier comprises: an input for receiving the synchronizing signal transmitted from the first oscillator; a second oscillator; an analog to digital converter coupled with the second oscillator and configured to digitize the captured EEG signals; and a microcontroller configured to control a frequency of the second oscillator and an operation of the analog to digital converter (ADC) based on the synchronizing signal.

Optionally, the first oscillator is configured to generate the synchronizing signal having a frequency in a range of 0.1 Hz to 10 kHz.

Optionally, the second oscillator is voltage controlled.

Optionally, the plurality of EEG sensors are configured to monitor intracranial EEG signals.

Optionally, the system further comprises a computing device in data communication with the plurality of amplifiers for processing the amplified EEG signals. Optionally, the system further comprises a display in data communication with the computing device for displaying the amplified EEG signals.

Optionally, the input comprises a signal isolator configured to receive the synchronizing signal. Optionally, the signal isolator comprises one or more isolated DC-DC power converters.

Optionally, the synchronizing signal has a frequency of 1 Hz.

Optionally, the microcontroller comprises a digital to analog (DAC) converter and the microcontroller is configured to adjust the second oscillator by setting the DAC to a corresponding voltage.

Optionally, the at least one amplifier further comprises an internal timer and the microcontroller is configured to measure the period of the synchronizing signal using the internal timer. Optionally, the internal timer has a resolution in a microsecond numerical range.

Optionally, the at least one amplifier further comprises a filter configured to filter out high frequency noise present in an analog voltage transmission from the microcontroller, wherein the high frequency noise has a frequency greater than 2 kHz.

Optionally, the at least one amplifier comprises at least one unique amplifier in dedicated data communication with each of the plurality of EEG sensors.

The present specification also discloses a method for synchronizing EEG signals measured by an EEG monitoring system, wherein the EEG monitoring system comprises a plurality of EEG sensors positioned on a layer of tissue and wherein each of the plurality of EEG sensors is configured to capture EEG signals of a patient, at least one amplifier coupled to each of the plurality of EEG sensors and configured to amplify the captured EEG signals, and a first oscillator, wherein the at least one amplifier comprises an input for receiving a synchronizing signal from the first oscillator, the method comprising: distributing the synchronizing signal from the first oscillator to each of the at least one amplifier; measuring a period of the synchronizing signal; adjusting a second oscillator, having a frequency, in the at least one amplifier to match a timer count based on the period of the synchronizing signal; determining a function of the frequency of the second oscillator frequency to produce a clock signal; and adjusting a frequency of each of the second oscillators such that the frequencies of the second oscillators are identical.

Optionally, the first oscillator is configured to generate the synchronizing signal having a frequency in a range of 0.1 Hz to 10 kHz.

Optionally, the second oscillator is voltage controlled.

Optionally, the function of the frequency of the second oscillator frequency is determined by dividing the frequency to produce the clock signal. Optionally, the method further comprises using the clock signal to drive the analog to digital converter clock signal. Optionally, the at least one amplifier comprises the second oscillator, the analog to digital converter coupled to the second oscillator and configured to digitize the captured EEG signals, and a microcontroller configured to control the frequency of the second oscillator and an operation of the analog to digital converter based on the synchronizing signal. Optionally, the microcontroller comprises a signal isolator wherein the signal isolator comprises isolated DC-DC power converters.

Optionally, the method further comprises transmitting the amplified EEG signals to a computing device, wherein the computing device is configured to process the amplified EEG signals.

Optionally, the synchronizing signal has a frequency of 1 Hz.

Optionally, the microcontroller includes a digital to analog (DAC) converter and the microcontroller is configured to adjust the second oscillator by setting the DAC to a corresponding voltage.

Optionally, the at least one amplifier further comprises an internal timer having microsecond resolution and the microcontroller is configured to measure a period of the synchronizing signal using the internal timer.

Optionally, the at least one amplifier further comprises a filter configured to filter out high frequency noise, having a value range greater than 2 kHz, present in an analog voltage signal from the microcontroller output.

The present specification also discloses a system for monitoring EEG signals comprising: a plurality of EEG sensors spatially positioned on a layer of tissue for capturing EEG signals of a patient; a plurality of amplifiers coupled with the EEG sensors for amplifying the captured signals; and a low frequency oscillator; wherein each amplifier comprises: an input for receiving a low frequency synchronizing signal from the low frequency oscillator wherein the low frequency synchronizing signal is configured to be distributed to each amplifier of the plurality of amplifiers; a voltage controlled oscillator; an analog to digital converter coupled with the voltage controlled oscillator for digitizing the captured signals; and a microcontroller for controlling a frequency of the voltage controlled oscillator and operation of the analog to digital converter (ADC) based on the synchronizing signal.

The system may be used to monitor intracranial EEG signals.

Optionally, the system further comprises a computing device in data communication with the plurality of amplifiers for processing the amplified signals. Optionally, the system further comprises a display in data communication with the computing device for displaying the amplified signals.

Optionally, the input comprises a signal isolator for receiving the synchronizing signal. The signal isolator may comprise isolated DC-DC power converters.

Optionally, the synchronizing signal has a frequency of 1 Hz.

Optionally, the microcontroller includes an internal digital to analog (DAC) converter wherein the microcontroller is configured to adjust the voltage controlled oscillator by setting the internal DAC to a corresponding voltage.

Optionally, each amplifier further comprises an internal timer with microsecond resolution wherein the microcontroller is configured to measure the period of the synchronizing signal using the internal timer.

Optionally, each amplifier further comprises a low pass filter configured to filter out high frequency noise on analog voltage from the microcontroller output.

The present specification also discloses a method for synchronizing EEG signals measured by a an EEG monitoring system, wherein the EEG monitoring system comprises a plurality of EEG sensors spatially positioned on a layer of tissue for capturing EEG signals of a patient, a plurality of amplifiers coupled with the EEG sensors for amplifying the captured signals, and a low frequency oscillator, wherein each amplifier comprises: an input for receiving a low frequency synchronizing signal from the low frequency oscillator wherein the low frequency synchronizing signal is configured to be distributed to each amplifier of the plurality of amplifiers; a voltage controlled oscillator; an analog to digital converter coupled with the voltage controlled oscillator for digitizing the captured signals; and a microcontroller for controlling a frequency of the voltage controlled oscillator and operation of the analog to digital converter (ADC) based on the synchronizing signal, the method comprising: distributing a low frequency synchronizing signal from the low frequency oscillator to each of the plurality of amplifiers; measuring a period of the low frequency synchronizing signal; adjusting the voltage controlled oscillator of an amplifier of the plurality of amplifiers to match a timer count based on the period of the low frequency synchronizing signal; dividing a voltage controlled oscillator frequency to produce analog to digital converter clock and convert start signals; and adjusting the frequency of each voltage controlled oscillator of each of the plurality of amplifiers such that the frequency of each voltage controlled oscillator is identical.

The method may be used to monitor intracranial EEG signals.

Optionally, the EEG monitoring system further comprises a computing device in data communication with the plurality of amplifiers for processing the amplified signals. Optionally, the EEG monitoring system further comprises a display in data communication with the computing device for displaying the amplified signals.

Optionally, each input comprises a signal isolator for receiving the synchronizing signal. The signal isolator may comprise isolated DC-DC power converters.

Optionally, the synchronizing signal has a frequency of 1 Hz.

Optionally, the microcontroller includes an internal digital to analog (DAC) converter wherein the microcontroller is configured to adjust the voltage controlled oscillator by setting the internal DAC to a corresponding voltage.

Optionally, each amplifier further comprises an internal timer with microsecond resolution wherein the microcontroller is configured to measure the period of the synchronizing signal using the internal timer.

Optionally, each amplifier further comprises a low pass filter configured to filter out high frequency noise on analog voltage from the microcontroller output.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1:
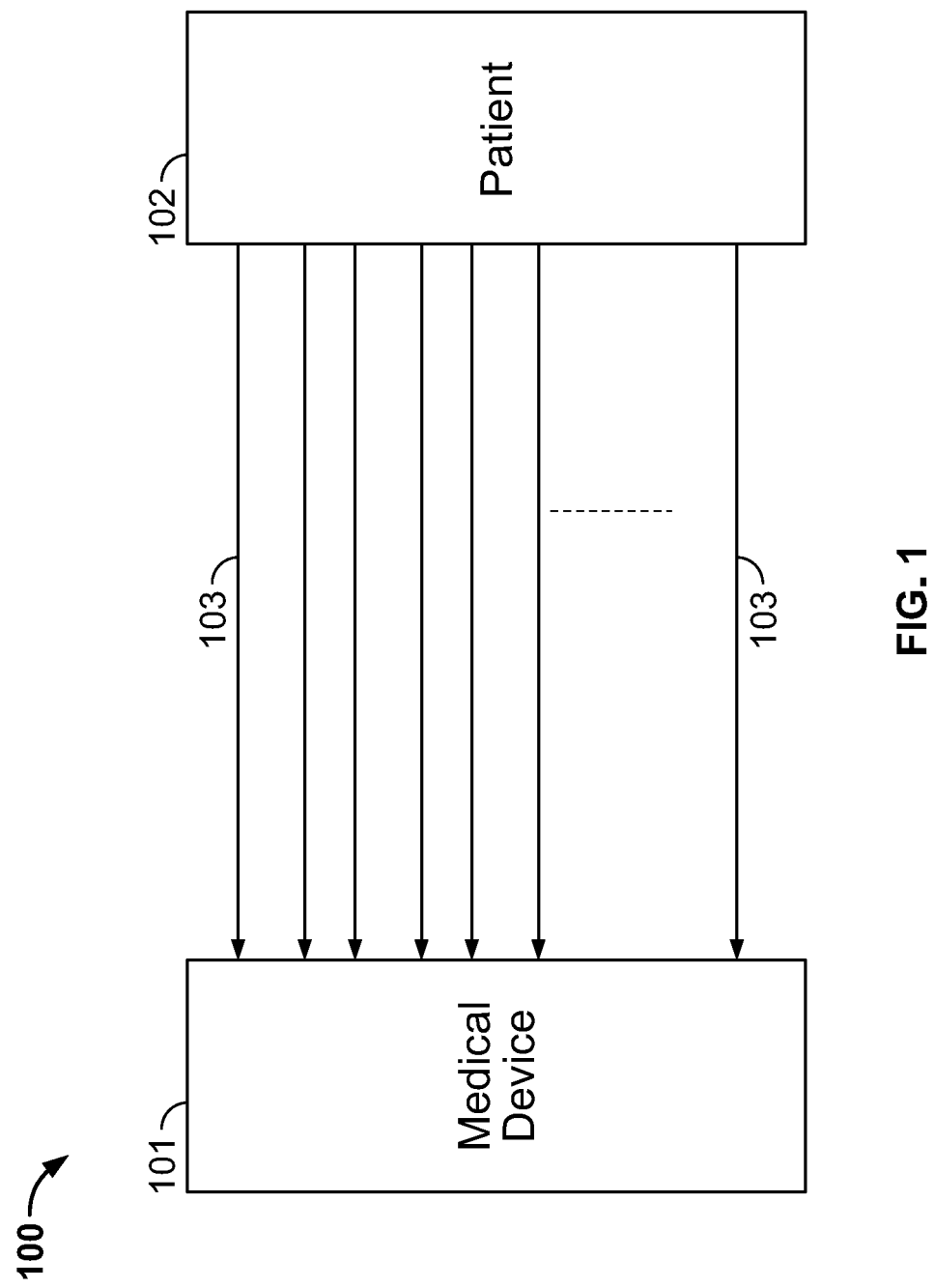
FIG. 1 shows a block diagram of a conventional medical system comprising a large number of electrodes deployed on a patient body.

The present specification enables synchronization of EEG data between two or more amplifiers using a low frequency synchronizing signal that is shared using low power circuits and standard cables. By using the method of the present specification, electromagnetic interferences are filtered out since the frequencies of the low speed shared signal and of the interferences do not overlap.

In various embodiments, the present specification provides a simple and low cost method of synchronizing the data acquisition of multiple amplifiers during EEG monitoring. This method eliminates the need for distributing data from a high speed clock to each of the multiple amplifiers, thereby eliminating the need for high power consumption and specialized components/cables.

In an embodiment, the method of the present specification comprises distributing a low frequency clock among a plurality of amplifiers for synchronizing the data acquired by said amplifiers during EEG monitoring. The low frequency clock uses single ended circuitry and cabling whereby high frequency electromagnetic interference can be filtered out from the clock signal.

In various embodiments, the methods and systems of the present specification enable the synchronizing of a sample rate of EEG data acquired on different devices (amplifiers) with only a low frequency synchronizing signal. In some embodiments, a low frequency synchronizing signal is transmitted to the devices to be synchronized, wherein the term low frequency, in the context of a synchronizing signal, refers to a range of 0.1 Hz to 10 kHz, with a preferred range of 0.5 Hz to 2 Hz. It should be appreciated that the 0.5 Hz to 2 Hz range leads to a more accurate synchronization process. Each device measures the period of the synchronizing signal using an internal timer with microsecond resolution. The device then adjusts its microcontroller clock so that the expected number of ticks occurs between the low frequency synchronizing signal edges (for example, 1,000, 000). This is done by adjusting the voltage to an external voltage-controlled oscillator in finite steps using a digital to analog converter (DAC) internal to the microcontroller. These adjustments can continue, to counter clock drift over time, in order to maintain synchronization.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and receiving data. Each "computing device" may be coupled to at least one display, which displays information about the patient parameters and the functioning of the system, by means of a GUI. The GUI also presents various menus that allow users to configure settings according to their requirements. The system further comprises at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit such as a patient's body. EEG electrodes are small metal discs, grids, strips or cylinders usually made of stainless steel, platinum, tin, gold or silver covered with a silver chloride coating. They are typically placed on the scalp on predetermined locations but may also be placed as intracranial electrodes directly on the surface of the brain or implanted into the brain to record electrical activity from the cerebral cortex.

An "electrode grid" is a thin sheet of material with multiple small (roughly a couple mm in size) recording electrodes implanted within it. These are placed directly on the surface of the brain and have the advantage of recording the EEG without the interference of the skin, fat tissue, muscle, and bone that may limit scalp EEG. Shapes and sizes of these sheets are chosen to best conform to the surface of the brain and the area of interest.

A "depth electrode" refers to small wires that are implanted within the brain itself. Each wire has electrodes which surround it. These electrodes are able to record brain activity along the entire length of the implanted wire. They have the advantage of recording activity from structures deeper in the brain. They can be implanted through small skin pokes.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

FIG. 1 shows a block diagram of a conventional medical system 100 comprising a large number of electrodes deployed on the body of a patient 102. The medical device 101 represents a conventional neuromonitoring medical system, such as an EEG (electroencephalography) system, which comprises a large number of electrodes for monitoring a neurological state of a patient for diagnosis and preventive treatment of certain diseases and for monitoring patients during anesthesia, among other procedures. As shown in FIG. 1, the medical device 101 is coupled to the patient 102 through a plurality of electrical leads 103 such that each of the leads 103 is coupled to an electrode (not shown) positioned at an appropriate location on the body of the patient 102.

Figure 2:
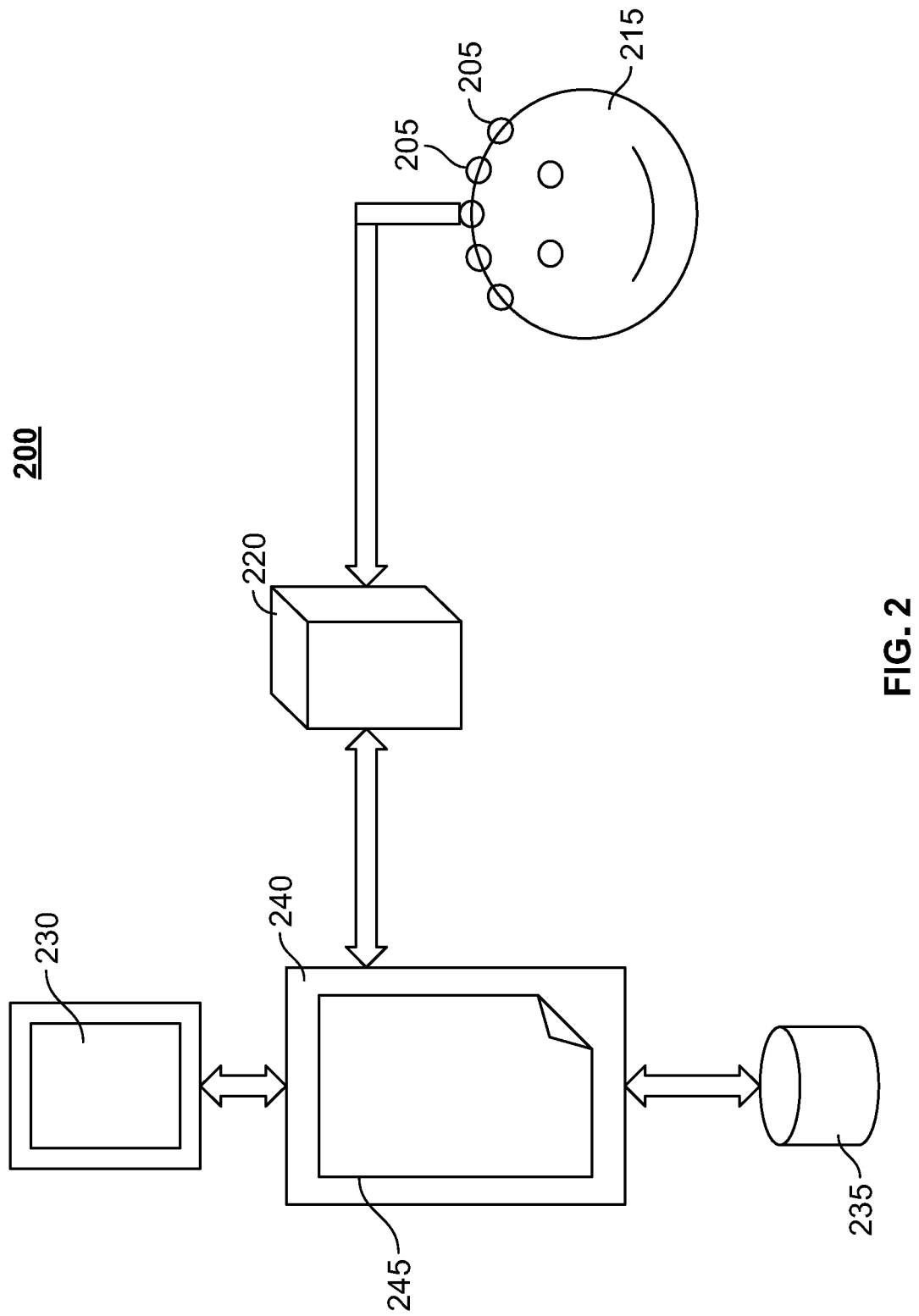
FIG. 2 illustrates an electroencephalography (EEG) system for detecting, diagnosing, or predicting neurological events from EEG signals, in accordance with some embodiments of the present specification.

FIG. 2 illustrates an electroencephalography (EEG) system 200 for detecting, diagnosing, or predicting neurological events from EEG signals, in accordance with some embodiments of the present specification. The figure shows a plurality of EEG sensors or electrodes 205 spatially positioned on a layer of tissue such as the scalp of a patient 215. In other embodiments, the plurality of electrodes is positioned intracranially, directly on the brain. For example, in some embodiments, the plurality of electrodes is placed on the brain by skull resection or via burr holes. The plurality of electrodes 205 are electrically connected with a multi-channel amplifier 220 that is in data communication with a computing device 240. The computing device 240 is in data communication with a display unit 230 and at least one database 235.

In various embodiments, the plurality of electrodes 205 are small metal discs, strips, grids, and/or cylinders typically made of stainless steel, platinum, tin, gold or silver covered with a silver chloride coating. The plurality of electrodes 205 sense electrical signals (EEG signals) from the patient's brain and conduct the analog signals over an electrical connection link to the multi-channel amplifier 220 that amplifies the signals, converts the signals from an analog EEG data set to a digital EEG data set, and communicates the resultant digital EEG signal to the computing device 240 over a communication link. In embodiments, the communication link may be wired or wireless links. In various embodiments, more than one amplifier 220 may be used for acquiring and amplifying the voltage sensed by the electrodes 205 in the EEG system.

The computing device 240 includes an input/output controller, at least one communications interface and system memory. The system memory includes at least one random access memory (RAM) and at least one read-only memory (ROM). These elements are in communication with a central processing unit (CPU) to enable operation of the computing device 240. In various embodiments, the computing device 240 may be a conventional standalone computer or alternatively, the functions of the computing device 240 may be distributed across multiple computer systems and architectures. For example, in a distributed architecture, the at least one database 235 and processing circuitry are housed in separate units or locations. Some units perform primary processing functions and contain at a minimum a general controller or a processing circuitry and a system memory.

The computing device 240 executes EEG software 245 that implements a plurality of programmatic instructions or code to process, store, retrieve and display, on the display unit 230, the patient's EEG data. In embodiments, the EEG software 245 processes the received digital EEG signals, extracts parameters that characterize the EEG data, and generates a display of the data for a user. The processed EEG data is either displayed on the display unit 230 in real-time or stored in at least one database 235 for later analyses.

In some embodiments, execution of sequences of programmatic instructions enables or causes the CPU to perform various functions and processes. In alternate embodiments, hard-wired circuitry may be used in place of, or in combination with, software instructions for implementation of the processes of systems and methods described in this specification. Thus, the systems and methods described are not limited to any specific combination of hardware and software.

Figure 3:
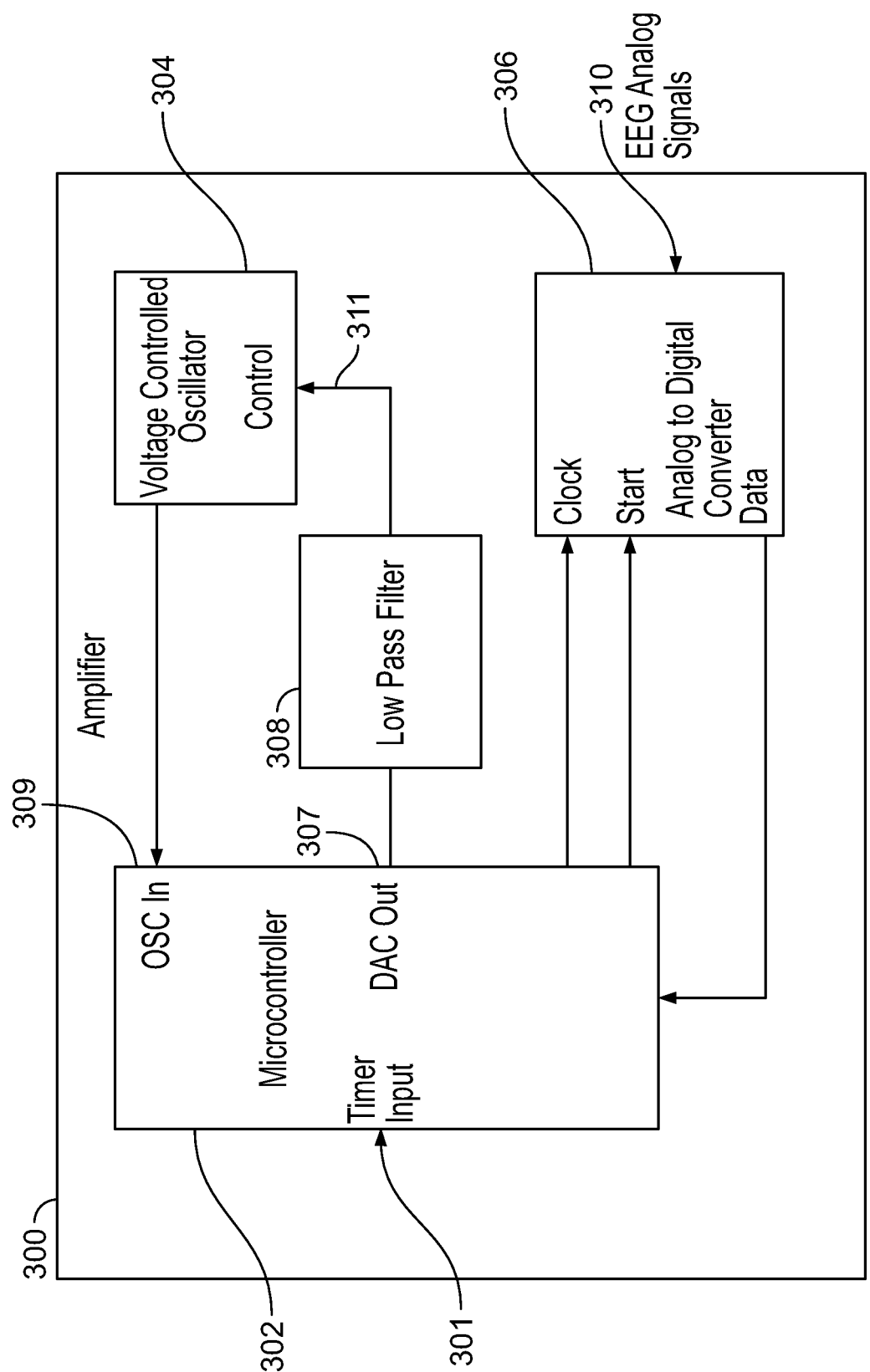
FIG. 3 is a block diagram illustrating an amplifier used for amplifying EEG signals recorded from a patient's brain, in accordance with an embodiment of the present specification.

FIG. 3 is a block diagram illustrating an amplifier 300 used for amplifying EEG signals recorded from a patient's brain, in accordance with an embodiment of the present specification. The amplifier 300 comprises a microcontroller 302, a voltage controlled oscillator 304, an analog-to-digital converter (ADC) 306 and a low pass filter 308. As shown, EEG analog signals 310 recorded from a patient's brain by using a plurality of EEG electrodes are transmitted to the ADC 306 which converts the input analog signals to digital signals for output to the microcontroller 302. The microcontroller 302 controls the operation of the voltage controlled oscillator 304 by controlling the voltage on the DAC output 307, thereby adjusting the frequency of the voltage controlled oscillator 304 to a predefined frequency. More specifically, the microcontroller 302, at the DAC output 307, modulates the voltage amplitude and/or frequency which, in turn, controls the frequency at which the voltage controlled oscillator 304 oscillates. The microcontroller 302 controls the ADC 306 by generating the clock and start signals of the ADC 306. The microcontroller 302 bases the control of the voltage control oscillator 304 and the ADC 306 on the input timer/frequency 301. The low pass filter 308 filters out high frequency noise above 2 kHz on the analog voltage from the microcontroller DAC output 307 so as to provide a useful DC signal input 311 to the oscillator 304 thereby enabling the oscillator 304 to produce a stable oscillator frequency at an oscillator (OSC) input 309 of the microcontroller 302.

Figure 4A:
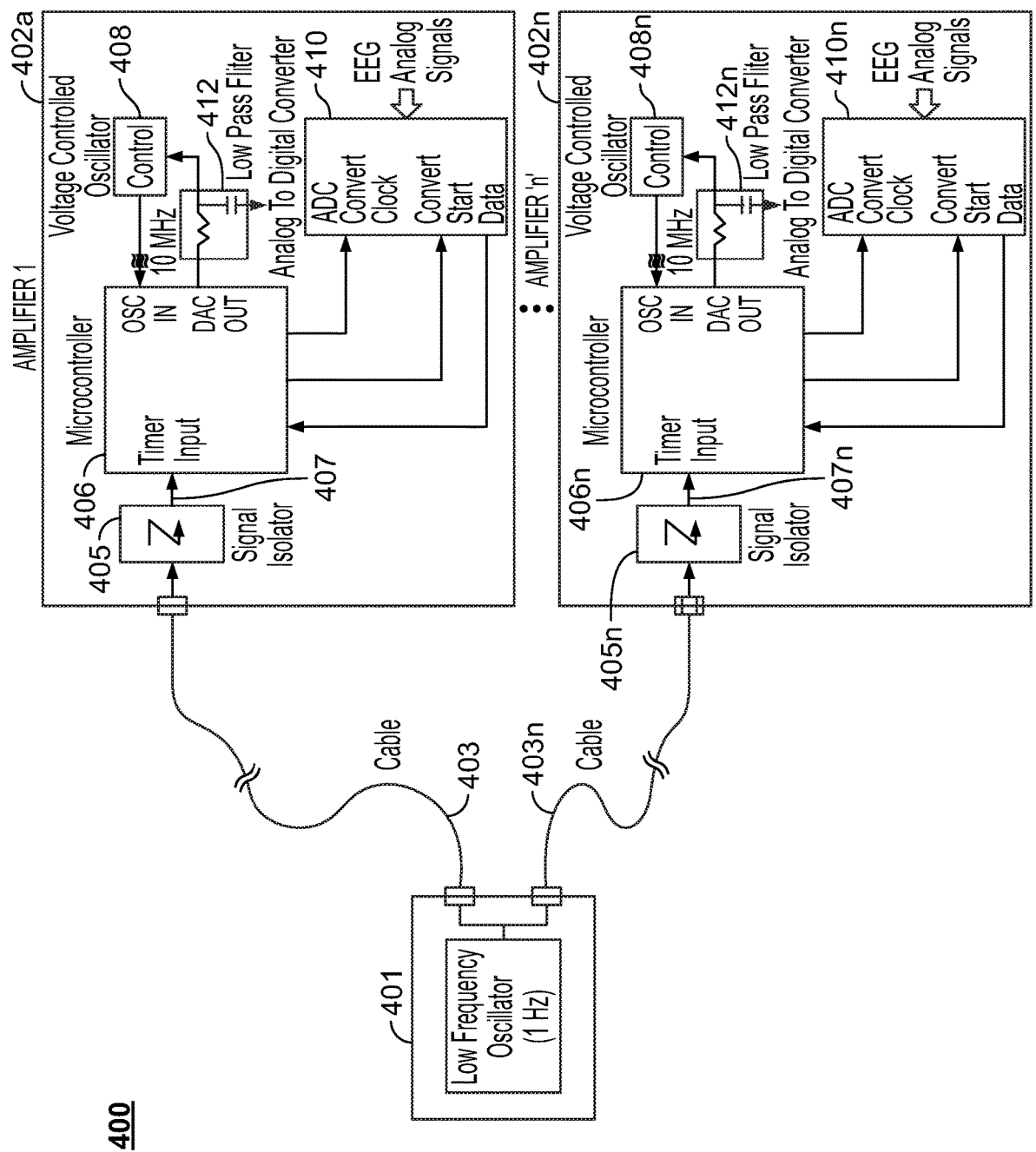
FIG. 4A is a block diagram illustrating a system comprising a plurality of amplifiers synchronized operatively for amplifying EEG signals recorded from a patient's brain, in accordance with an embodiment of the present specification.

FIG. 4A is a block diagram illustrating a system 400 comprising a plurality of amplifiers synchronized operatively for amplifying EEG signals recorded from a patient's brain, in accordance with an embodiment of the present specification. Each of the plurality of amplifiers 402a through 402n comprises a signal isolator 405, a microcontroller 406, a voltage controlled oscillator 408, an analog to digital converter 410 and a low pass filter 412. As shown, a low frequency oscillator 401 provides a low frequency synchronizing signal which is distributed to each of the plurality of amplifiers 402a through 402n that operate in conjunction to amplify and digitize intracranial EEG signals. In some embodiments, the synchronizing signal has a frequency in a range of 0.1 Hz to 10 kHz, more preferably in a range of 0.5 Hz to 2 Hz, and most preferably around 1 Hz.

In some embodiments, the low frequency oscillator 401 is external to the amplifiers 402a through 402n. Each signal isolator 405, associated with each of the plurality of amplifiers 402a through 402n, electrically isolates each of the plurality of amplifiers 402a through 402n from ground. In some embodiments, each signal isolator 405 comprises isolated DC-DC power converters and provides an isolation barrier over which a low frequency signal can be easily coupled. Each voltage controlled oscillator 408 provides a master clock to the microcontroller 406 of its respective amplifier. In various embodiments, any synchronizing signal frequency may be provided by the low frequency oscillator 401. However, a synchronizing signal frequency lower than 1 Hz increases the time taken to synchronize the signal while a synchronizing signal frequency higher than 1 Hz requires more microcontroller resources.

In embodiments, cables 403 are used to supply the synchronizing signal from the low frequency oscillator 401 to each of the plurality of amplifiers 402a through 402n. In an embodiment, the synchronizing signal is carried by a 28AWG cable/conductor. In alternate embodiments, cables having other AWG values may also be used.

During operation, a microcontroller 406 of each of the amplifiers 402a through 402n receives the 1 Hz synchronizing signal from the low frequency oscillator 401 via a timer input 407 and measures the period of the 1 Hz synchronizing signal using an internal timer. In some embodiments, the internal timer measures the period of the 1 Hz synchronizing signal with microsecond resolution. The microcontroller 406 then adjusts an operational frequency of the voltage controlled oscillator 408 by setting its internal DAC to a voltage value within a predefined range until the measured period of the synchronizing signal at timer input 407 matches a defined timer count based on the expected period of the synchronizing signal.

In some embodiments, the synchronization signal is a square wave with a frequency of 1 Hz and 50% duty cycle (high for half of the period, low for half of the period). The square wave is defined by "signal edges" referring to the rising edges of the square wave. Alternatively, "signal edges" may also refer to the falling edges of the square wave. In embodiments, one million "ticks" occur in a timer since a previous 1 Hz sync edge. In embodiments, if a timer is operated with microsecond resolution and the value of the timer is captured at each rising edge of the 1 Hz synchronization signal, one would expect a delta of 1,000,000 between consecutive timer captures since there are 1,000,000 microseconds in 1 second (1 Hz). Since the voltage controlled oscillator 408 is providing the master clock to the microcontroller 406, adjusting the operational frequency of the voltage controlled oscillator 408 will adjust the frequency of all microcontroller clocks and timing signals produced by the microcontroller 406. The microcontroller 406 adjusts the operational frequency of the voltage controlled oscillator 408 by setting the internal DAC of the microcontroller 406 to a certain voltage value which is then sent to the voltage controlled oscillator 408 by the microcontroller 406. In embodiments, to maintain synchronization, the adjustments of the operational frequency of the voltage controlled oscillator 408 continue as the clocks drift over time and temperature. In some embodiments, the internal DAC of the microcontroller 406 is set to a voltage value in a range of 0 to 3.3 V.

Thereafter, the operational frequency of the voltage controlled oscillator 408 is divided by the microcontroller 406 to produce clock and 'convert start' signals of the analog to digital converter (ADC) 410. Both the clock and 'convert start' signals determine the sample rate and timing of the analog to digital conversion within the ADC 410. Thus, the ADC 410 is synchronized to the 1 Hz signal.

Each microcontroller 406 in each of the other amplifiers 402n adjusts the frequency of its associated voltage controlled oscillator so that its frequency is identical to the frequency of the voltage controlled oscillator 408. In some embodiments, the voltage controlled oscillator 408 can be adjusted after multiple 1 Hz synchronizing signal periods or at any other frequency interval that results in a desired accuracy of synchronization of the amplifiers. For example, in an embodiment, the microcontroller 406 counts, using its internal timer, the number of microsecond ticks that occur over four 1 Hz synchronizing signal periods and adjust its clock until it reaches the desired count. This allows for greater accuracy of synchronization but with a tradeoff of more time elapsed to reach synchronization.

Without the voltage controlled oscillator 408, the use of low frequency synchronizing signal is restricted to an accuracy of approximately 10 μsec of synchronization using calculations done on a host PC system for time-stamped data and stimulations. The microcontroller clocks are allowed to drift in this timing scheme with the host PC correcting the timestamps for the calculated drift. With the addition of the voltage controlled oscillator 408 and the method of measuring and compensating for oscillator inaccuracy, synchronization better than 1 μsec is achieved at the microcontroller clock level. This tighter frequency accuracy is necessary to avoid beat frequencies.

Figure 4B:
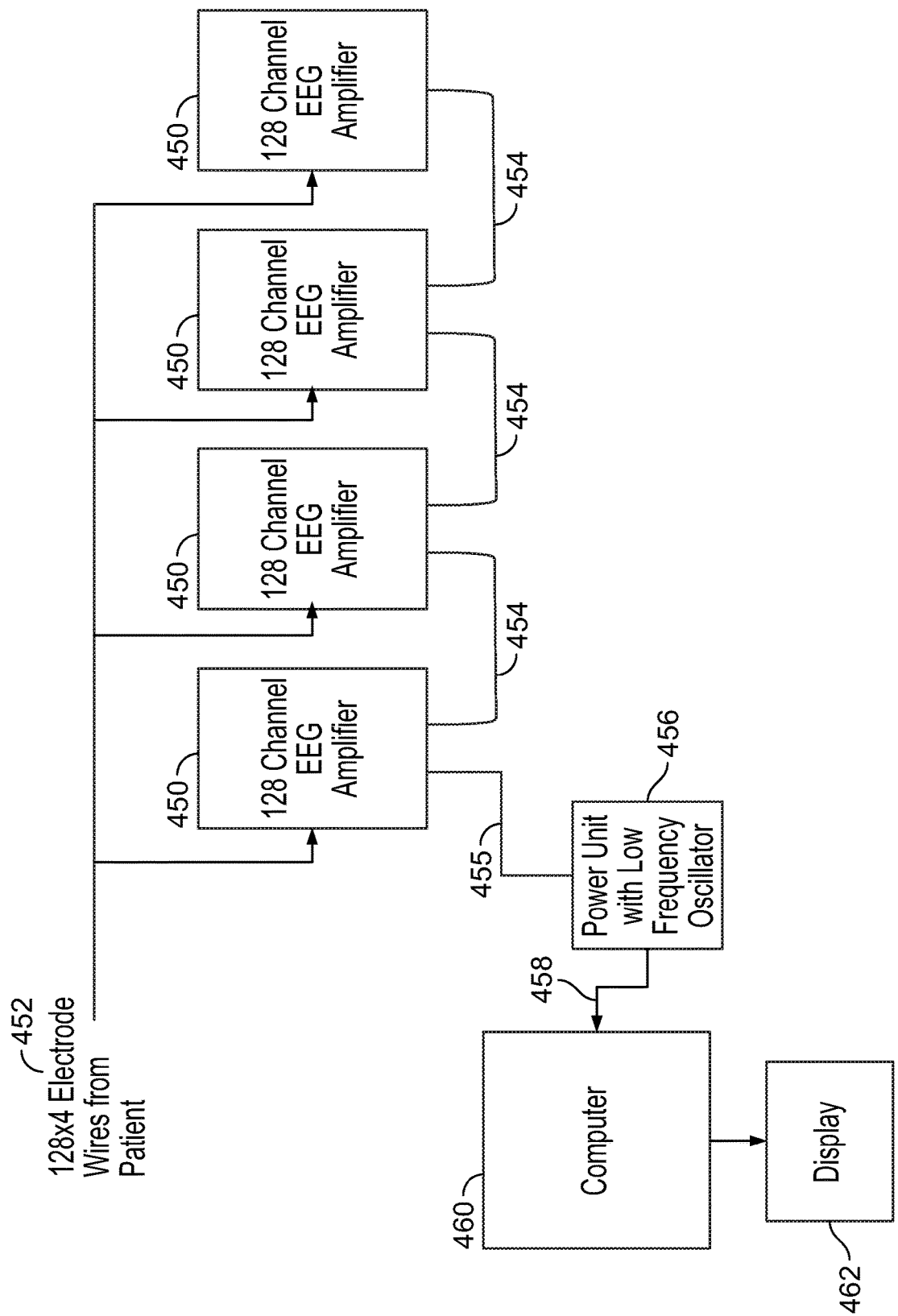
FIG. 4B illustrates a block diagram of an EEG system incorporating a plurality of amplifiers, in accordance with an embodiment of the present specification.

FIG. 4B illustrates a block diagram of an EEG system incorporating a plurality of amplifiers, in accordance with an embodiment of the present specification. Referring to FIG. 4B, a plurality of 128 channel amplifiers 450 receive input EEG signals via 128x4 electrode wires captured by a plurality of electrodes 452 connected to a patient. Digitized and amplified signals travel via a plurality of power/signal synchronization cables 454 between each of the plurality of amplifiers 450. A first power/signal synchronization cable 455 carries the digitized and amplified signal communicated between each of the plurality of amplifiers 450 to a power unit comprising a low frequency oscillator 456 which is used to synchronize the signals received from the plurality of amplifiers 450. The synchronized signals are transferred via data cables 458 to a computing device 460 (similar to computing device 240 described with reference to FIG. 2A) and are displayed for analysis on a display device 462 coupled with the computing device 460.

Figure 5:
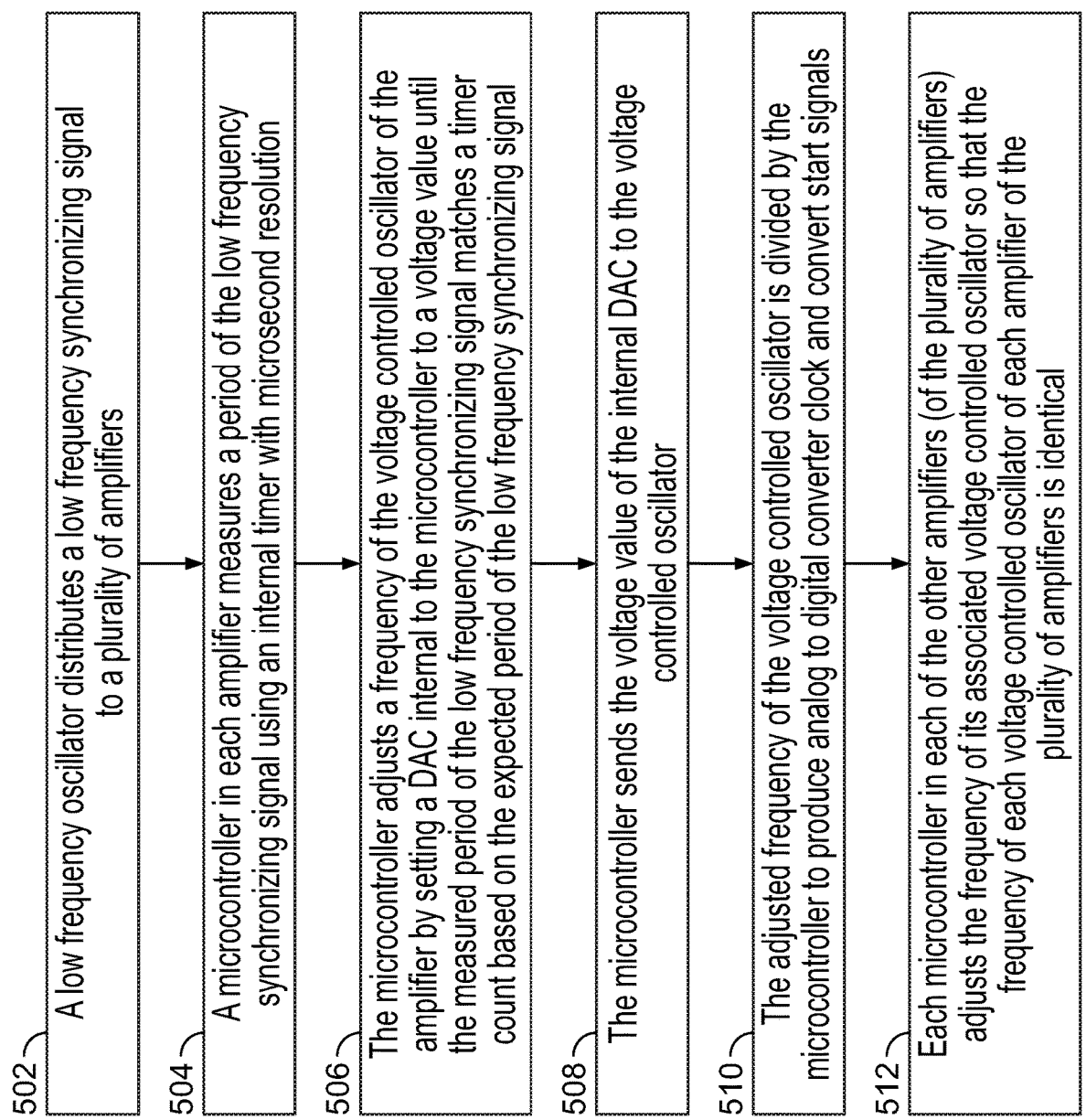
FIG. 5 is a flowchart illustrating the steps involved in a method of distributing a low frequency signal to a plurality of synchronized amplifiers to measure EEG signals, in accordance with an embodiment of the present specification.

FIG. 5 is a flowchart illustrating a plurality of exemplary steps involved in a method of distributing a low frequency signal to a plurality of amplifiers for synchronization and to measure EEG signals, in accordance with an embodiment of the present specification. At step 502, a low frequency oscillator of an EEG monitoring system of the present specification distributes a low frequency synchronizing signal to a plurality of amplifiers that are in data communication with the low frequency oscillator. In some embodiments, the low frequency synchronizing signal is a 1 Hz synchronizing signal.

At step 504, a microcontroller in each of the plurality of amplifiers measures a period of the low frequency synchronizing signal using an internal timer. In some embodiments, the internal timer measures the period of the low frequency synchronizing signal with microsecond resolution. The microcontroller then adjusts an operational frequency of a voltage controlled oscillator of the amplifier by setting an internal DAC of the microcontroller to a voltage value, at step 506, until the measured period of the low frequency synchronizing signal matches a timer count based on the expected period of the low frequency synchronizing signal. At step 508, the microcontroller sends the voltage value of the internal DAC to the voltage controlled oscillator to enable the voltage controlled oscillator to produce a stable frequency to at an oscillator (OSC) input of the microcontroller.

At step 510, the adjusted operational frequency of the voltage controlled oscillator is divided by the microcontroller to produce clock and convert start signals of an analog to digital converted (ADC) of the amplifier. Finally, at step 512, each microcontroller in each of the other amplifiers (of the plurality of amplifiers) adjusts the frequency of its associated voltage controlled oscillator so that the frequency of each voltage controlled oscillator of each amplifier of the plurality of amplifiers is identical. In some embodiments, the frequency adjustment occurs at twice the low frequency synchronizing signal or at any interval that will result in the desired accuracy of synchronization of the amplifiers.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A system for monitoring EEG signals comprising:
    a plurality of EEG sensors, wherein each of the plurality of EEG sensors is configured to capture EEG signals of a patient;
    a plurality of amplifiers, wherein each of the plurality of amplifiers is coupled to at least one of the plurality of EEG sensors and wherein each of the plurality of amplifiers is configured to amplify the captured EEG signals; and
    a first oscillator configured to generate a synchronizing signal;
        wherein each of the plurality of amplifiers comprises:
            an input for receiving the synchronizing signal transmitted from the first oscillator;
            a second oscillator;
            an analog to digital converter coupled with the second oscillator and configured to digitize the captured EEG signals; and
            a microcontroller configured to control a frequency of the second oscillator and an operation of the analog to digital converter (ADC) based on the synchronizing signal.

2. The system of claim 1, wherein the first oscillator is configured to generate the synchronizing signal having a frequency in a range of 0.1 Hz to 10 kHz.

3. The system of claim 1, wherein the second oscillator is configured to be voltage controlled.

4. The system of claim 1, wherein the plurality of EEG sensors are configured to monitor intracranial EEG signals.

5. The system of claim 1, further comprising a computing device in data communication with each of the plurality of amplifiers for processing the amplified captured EEG signals.

6. The system of claim 5, further comprising a display in data communication with the computing device for displaying the amplified captured EEG signals.

7. The system of claim 1, wherein the input comprises a signal isolator configured to receive the synchronizing signal.

8. The system of claim 7, wherein the signal isolator comprises one or more isolated DC-DC power converters.

9. The system of claim 1, wherein the synchronizing signal has a frequency of 1 Hz.

10. The system of claim 1, wherein the microcontroller comprises a digital to analog (DAC) converter and wherein the microcontroller is configured to adjust the second oscillator by setting the DAC to a corresponding voltage.

11. The system of claim 1, wherein each of the plurality of amplifiers further comprises an internal timer and wherein the microcontroller is configured to measure the period of the synchronizing signal using the internal timer.

12. The system of claim 11, wherein the internal timer has a resolution in a microsecond numerical range.

13. The system of claim 1, wherein each of the plurality of amplifiers further comprises a filter configured to filter out high frequency noise present in an analog voltage transmission from the microcontroller, and wherein the high frequency noise has a frequency greater than 2 kHz.

14. The system of claim 1, wherein each of the plurality of amplifiers comprises a at least one unique amplifier in dedicated data communication with each of the plurality of EEG sensors.

15. The system of claim 1, wherein the microcontroller is configured to determine a function of the frequency of the second oscillator is determined by dividing the frequency to produce a clock signal.

16. The system of claim 15, wherein the microcontroller is configured to use the clock signal to drive an analog to digital converter clock signal.

* * * * *